(12) United States Patent
Sjöholm et al.

(10) Patent No.: US 9,132,044 B2
(45) Date of Patent: Sep. 15, 2015

(54) METHOD AND SYSTEM FOR DETECTING MOISTURE AT AN ABSORBENT ARTICLE

(75) Inventors: Johan Sjöholm, Lund (SE); Christofer Lundin, Flyinge (SE); Olle Hydbom, Lund (SE)

(73) Assignee: Pampett AB, Lund (SE)

( * ) Notice: Subject to any disclaimer, the term of this patent is extended or adjusted under 35 U.S.C. 154(b) by 330 days.

(21) Appl. No.: 13/500,492

(22) PCT Filed: Oct. 5, 2010

(86) PCT No.: PCT/SE2010/051073
§ 371 (c)(1),
(2), (4) Date: May 7, 2012

(87) PCT Pub. No.: WO2011/043724
PCT Pub. Date: Apr. 14, 2011

(65) Prior Publication Data
US 2012/0216607 A1     Aug. 30, 2012

(30) Foreign Application Priority Data
Oct. 7, 2009    (SE) ........................................ 0901286

(51) Int. Cl.
*G01N 5/02*     (2006.01)
*G01N 25/56*    (2006.01)
(Continued)

(52) U.S. Cl.
CPC ....... *A61F 13/42* (2013.01); *A61F 2013/15056* (2013.01); *A61F 2013/424* (2013.01)

(58) Field of Classification Search
CPC .............................. G01N 19/36; G01N 27/233
USPC ............................................................ 73/74
See application file for complete search history.

(56) References Cited

U.S. PATENT DOCUMENTS 6,362,738 B1 *   3/2002   Vega ........................ 340/572.1
6,677,859 B1     1/2004   Bensen
(Continued)

FOREIGN PATENT DOCUMENTS

DE        10144022 A1     3/2003
GB         2449669 A     12/2008
(Continued)

OTHER PUBLICATIONS

Extended European Search Report dated Jul. 29, 2013, issued in European Application No. 10822322.3.
(Continued)

*Primary Examiner* — Hezron E Williams
*Assistant Examiner* — Rodney T Frank
(74) *Attorney, Agent, or Firm* — Harness, Dickey & Pierce, P.L.C.

(57) ABSTRACT

A system is provided for detecting moisture at an absorbent article. The system includes a device arranged to be attached on the absorbent article and a resonance circuit including a moisture sensitive part, wherein the resonance circuit has a first resonance frequency when the moisture sensitive part is in a dry condition and a second resonance frequency when the moisture sensitive part is in a moist condition. The system further includes a monitoring unit being arranged to transmit a test signal to the device, receive a response signal from the device, determine a frequency of the response signal and generate a detection signal if the determined frequency corresponds to the second resonance frequency. There is also provided a method for detecting moisture at a device attached on an absorbent article.

16 Claims, 4 Drawing Sheets

(51) Int. Cl.
*A61F 13/42* (2006.01)
*A61F 13/15* (2006.01)

(56) References Cited

U.S. PATENT DOCUMENTS

| | | | |
|---|---|---|---|
| 6,753,783 B2 * | 6/2004 | Friedman et al. | 340/573.7 |
| 6,774,800 B2 * | 8/2004 | Friedman et al. | 340/573.5 |
| 6,832,507 B1 | 12/2004 | Van de Berg et al. | |
| 7,071,830 B2 | 7/2006 | Sahlberg et al. | |
| 7,176,344 B2 | 2/2007 | Gustafson et al. | |
| 2002/0070868 A1 | 6/2002 | Jeutter et al. | |
| 2002/0089049 A1 | 7/2002 | Leduc et al. | |
| 2002/0145525 A1 | 10/2002 | Friedman et al. | |
| 2002/0145526 A1 | 10/2002 | Friedman et al. | |
| 2004/0036484 A1 | 2/2004 | Tamai | |
| 2004/0064114 A1 | 4/2004 | David et al. | |
| 2008/0300559 A1 | 12/2008 | Gustafson et al. | |

FOREIGN PATENT DOCUMENTS

| | | |
|---|---|---|
| JP | 2002071584 A | 3/2002 |
| WO | WO-0079497 A1 | 12/2000 |
| WO | WO 01/25472 A1 | 4/2001 |
| WO | WO 2004/021944 A1 | 3/2004 |
| WO | WO 2005/119195 | 12/2005 |
| WO | WO-2007038990 A1 | 4/2007 |
| WO | WO 2007/069968 A1 | 6/2007 |
| WO | WO-2007069945 A1 | 6/2007 |
| WO | WO 2008/069753 A1 | 6/2008 |
| WO | WO 2008/076005 A1 | 6/2008 |
| WO | WO 2008/130298 A1 | 10/2008 |
| WO | WO 2011/005096 A1 | 1/2011 |

OTHER PUBLICATIONS

Product sheets from Sensible Solutions Sweden AB (Jul. 1, 2009).
J. Sidén, e t al., "The 'Smart' Diaper Moisture Detection System," *Microwave Symposium Digest*, vol. 2, pp. 659-662 (Jun. 6-11, 2004).
C. Grimes, et al., "Wireless Magnetoelastic Resonance Sensors: A Critical Review," *Sensors*, vol. 2, pp. 294-313 (2002).
International Search Report, Jan. 13, 2011.

* cited by examiner

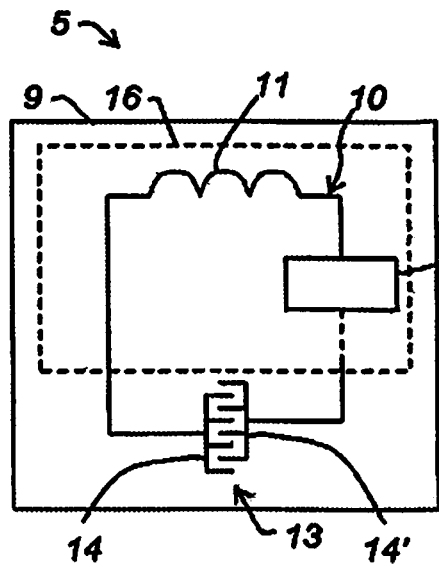
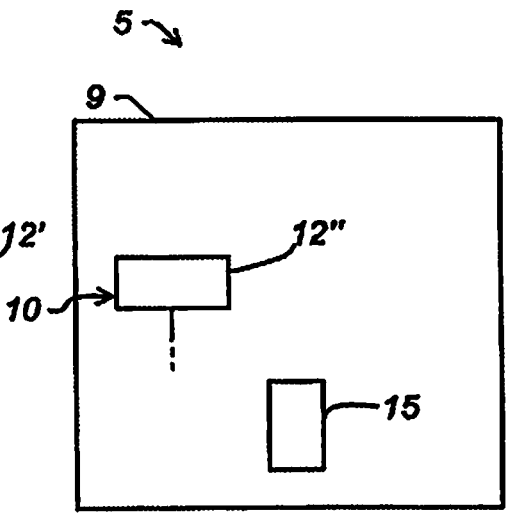
Fig. 2a      Fig. 2b
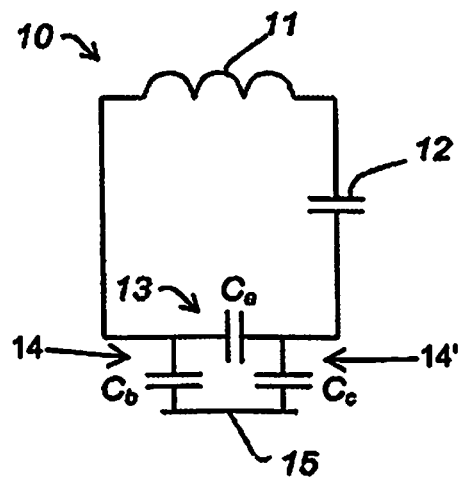
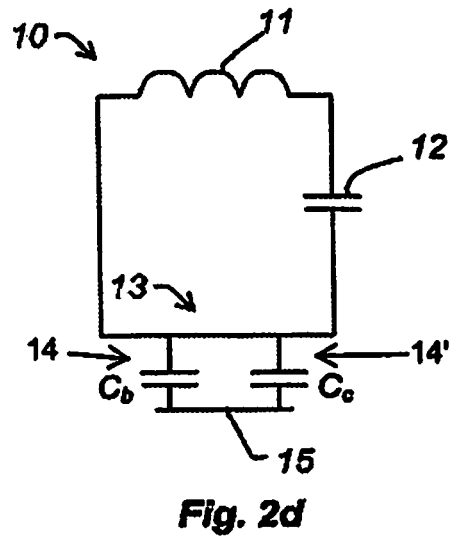
Fig. 2c      Fig. 2d

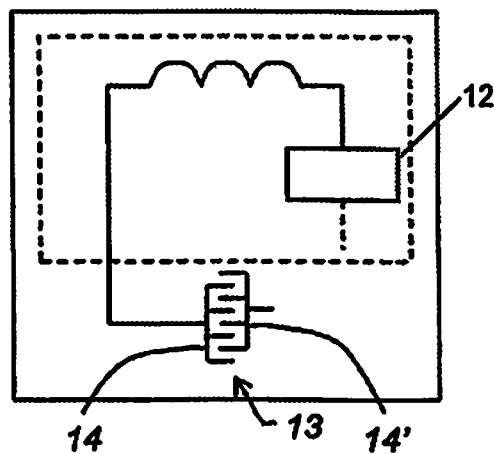
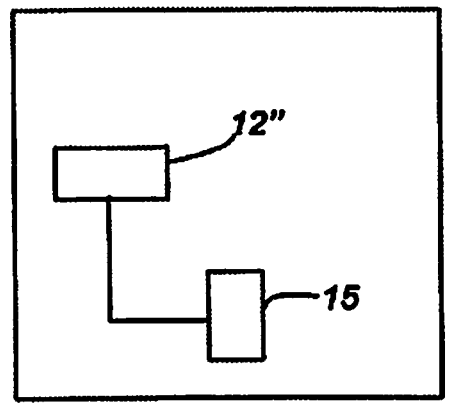
Fig. 3a  Fig. 3b
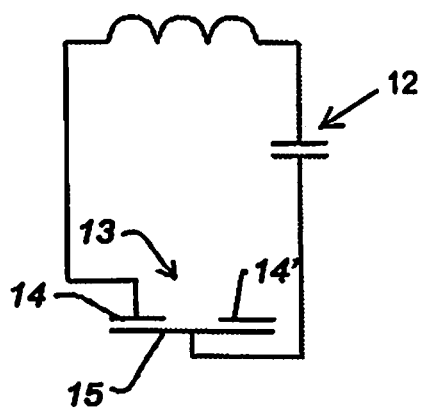
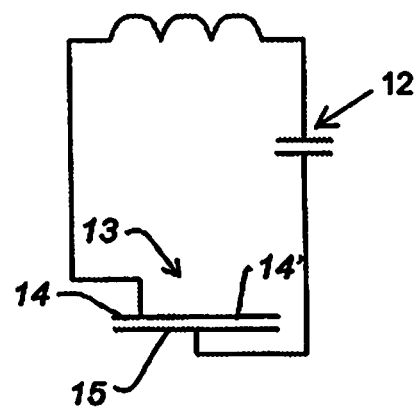
Fig. 3c  Fig. 3d

METHOD AND SYSTEM FOR DETECTING MOISTURE AT AN ABSORBENT ARTICLE

TECHNICAL FIELD

The present inventive concept generally relates to moisture detection. More specifically, the present inventive concept relates to a system and a method for detecting moisture at an absorbent article.

BACKGROUND OF THE INVENTION

Moisture detection is important in a number of different situations. One such situation is in relation to absorbent articles, such as diapers. In the prior art, there exists solutions for alerting e.g. nursing staff upon detection of moisture in a diaper of a wearer, whereby the nursing staff knows that it is time to change the diaper.

WO 2007/069945 discloses a wetness detecting means comprising an electrical circuit which is integrally formed into an absorbent article, such as a diaper. However, this wetness detecting means may be unpractical and uneconomical since it requires integration with the diaper and hence specially made diapers.

Thus, there is a need in the prior art for a convenient, reliable and economical solution for detecting moisture in absorbent articles.

SUMMARY OF THE INVENTION

In view of the above, an objective of the present inventive concept is to provide an improved system and method for detecting moisture at an absorbent article.

According to a first aspect of the inventive concept, there is provided a system for detecting moisture at an absorbent article, the system comprising a device arranged to be attached on the absorbent article and comprising a resonance circuit including a moisture sensitive part, wherein the resonance circuit has a first resonance frequency when the moisture sensitive part is in a dry condition and a second resonance frequency when the moisture sensitive part is in a moist condition. The system further comprising a monitoring unit being arranged to transmit a test signal to the device, receive a response signal from the device, determine a frequency of the response signal and generate a detection signal if the determined frequency corresponds to the second resonance frequency.

According to one embodiment, the system may be arranged to detect moisture at, on or in the absorbent article. The absorbent article may be any one of a diaper, an incontinence garment, a sanitary pad, a tampon a bandage, a bed protector or the like.

In this context, a dry condition relates to a condition wherein no soiling at the device has occurred. Moreover, a moist condition relates to a condition wherein soiling has occurred. The soiling may be release of moisture or fluid due to urination, evacuation of the bowel or other bodily waste.

By providing a device having a first and a second resonance frequency depending on the presence of moisture, moisture may be reliably detected. Moreover, by determining the frequency of the response signal the detection may be relatively insensitive to variations in the signal strength of the incoming signal e.g. due to varying distance between the device and the antenna or objects in the signal path dampening the test signal and the response signal.

Moreover, by generating the detection signal based on the presence of a signal at the second resonance frequency, generation of false detection signals due to absence of a device in an absorbent article may be avoided.

By attaching the device on the absorbent article, the device may be used in a plurality of different absorbent articles with a minimum of adaption. For example, the device may be attached by sewing, stitching, adhesion or similar. Hence, the inventive system does not require specially made or customized absorbent articles. A further advantage is that the device may be provided on different locations of the absorbent article. The sensitivity of the detection may hence be varied on an individual basis. For example, in case the absorbent article is a diaper the device may be attached on different locations in the diaper for different wearers.

According to one embodiment, the device comprises a fabric layer. The fabric layer may be provided as an outer layer on the device, facing the wearer of the absorbent article. This may increase the comfort for the wearer.

According to one embodiment, the moisture sensitive part comprises an absorption layer arranged to absorb moisture. By absorbing the moisture, the moisture may be retained at the moisture sensitive part. The frequency shift from the first to the second resonance frequency may hence be maintained whereby moisture may be detected also a while after the moisture has been released in the absorbent article.

According to one embodiment, the absorption layer includes a polymer. Especially, the polymer may be a polyacrylic acid.

According to one embodiment, the device comprises a moisture barrier covering at least a portion of the resonance circuit. Especially, the moisture barrier does not cover at least a part of the moisture sensitive part. The moisture barrier prevents circuit parts other than the moisture sensitive part from coming into contact with moisture and thus prevents unpredictable resonance frequency shifts.

According to one embodiment, the moisture sensitive part is arranged to shift the resonance frequency of the resonance circuit from the first resonance frequency to the second resonance frequency in the moist condition. Especially, the moisture sensitive part may provide this frequency shift by presenting a first capacitance in the dry condition and a second capacitance in the moist condition.

According to one embodiment, the moisture sensitive part comprises two conductors separated by an insulator. The two conductors may be arranged in parallel. In the dry condition, the two conductors may provide a capacitive contribution to the resonance circuit. In the moist condition, fluid (e.g. water) and any charge carriers (e.g. ions) therein may lower the impedance between the two conductors. The resonance frequency may thereby be shifted from a first to a second resonance frequency.

According to one embodiment, the two conductors form an interdigital finger structure. This structure provides a plurality of parallel conductors and thus enables a device with a large moist sensitive area and a high sensitivity to moist.

According to one embodiment the device comprises an electrically insulating layer having a first side and a second side, wherein the two conductors are provided on the first side and the moisture sensitive part further comprises a third conductor which is provided on the second side opposite to the two conductors and is arranged to be capacity-coupled to the two conductors. The moisture sensitive part may thus present a first capacitance between the two conductors provided on the first side, a second capacitance between the third conductor and the first of the two conductors provided on the first side, and a third capacitance between the third conductor and the second of the two conductors provided on the first side. In a dry condition, the resonance frequency of the resonance circuit may thus be defined by the first capacitance connected in parallel with the series connected second and third capacitances and any further capacitances or inductances of the resonance circuit. However, in a moist condition the resonance frequency of the resonance circuit may be defined mainly by these further capacitances or inductances of the resonance circuit. As a result, a reliable shift from a first resonance frequency in a dry condition to a second resonance frequency in a moist condition may be achieved. This inventive design of the device is particularly suitable for the frequency based moisture detection in accordance with the present inventive concept.

According to one embodiment, the device comprises a substance which is provided at the two conductors provided on the first side, the substance forming charge carriers when dissolved. These charge carriers may increase the sensitivity of the device. Especially, the substance may be a salt such as sodium chloride.

According to one embodiment, the resonance circuit comprises an inductor and a capacitor.

According to one embodiment, the test signal comprises at least one pulse. By transmitting a pulsed test signal the power consumption of the monitoring unit may be reduced.

According to one embodiment, the first resonance frequency is outside a frequency band or bandwidth of the test signal. According to this embodiment, the device may respond strongly to the test signal in a moist condition. This may reduce the risk of false detections.

According to an alternative embodiment, the first frequency is inside a frequency band or bandwidth of the test signal. According to this embodiment, the device may respond to the test signal both in a moist and a dry condition. A shorter pulse length of the alternative embodiment implies reduced power consumption of the monitoring unit.

According to one embodiment, the system further comprises an antenna connected to the monitoring unit. The test signal is transmitted through the antenna. Additionally, the response signal may be received through the antenna. The antenna may thus be used both for transmitting the test signal and for receiving the response from the device. This may simplify handling of the system and reduce the costs of the system.

According to one embodiment, the monitoring unit is arranged to reduce residual oscillations in the antenna, the oscillations generated by the test signal. This may facilitate detection of response signals from the device and increase the reliability of the moisture detection.

According to one embodiment, the monitoring unit is further arranged to determine an envelope of the response signal, and generate the detection signal if the envelope matches a reference envelope and if a determined frequency of the response signal corresponds to the second resonance frequency. If a received signal presents an expected envelope and has a frequency corresponding to the second resonance frequency, it may be determined that the received signal likely originates from the device and not from any other source. False detections due to noise at the second resonance frequency may hence be avoided.

According to a second aspect of the inventive concept, there is provided a method for detecting moisture at a device attached on an absorbent article, said device comprising a resonance circuit including a moisture sensitive part, the resonance circuit having a first resonance frequency when the moisture sensitive part is in a dry condition and a second resonance frequency when the moisture sensitive part is in a moist condition. The method comprising transmitting a test signal to the device, receiving a response signal from the device, determining a frequency of the response signal, and generating a detection signal if the determined frequency corresponds to the second resonance frequency.

The details and advantages discussed in relation to the first aspect apply correspondingly to the second aspect whereby reference hereby is made to the previous discussion.

BRIEF DESCRIPTION OF THE DRAWINGS

The above, as well as additional objects, features and advantages of the present inventive concept, will be better understood through the following illustrative and non-limiting detailed description of preferred embodiments of the present inventive concept, with reference to the appended drawings, where like reference numerals will be used for like elements, wherein:

FIGS. 2a and b illustrate the upper side and the underside, respectively, of a device in accordance with the first embodiment of the inventive concept.

FIGS. 2c and d illustrate a resonance circuit in a dry condition and in a moist condition, respectively, in accordance with a first embodiment of the inventive concept.

FIGS. 3a and b illustrate the upper side and the underside, respectively, of a device in accordance with an alternative embodiment of the inventive concept.

FIGS. 3c and d illustrate a resonance circuit in a dry condition and in a moist condition, respectively, in accordance with an alternative embodiment of the inventive concept.

DETAILED DESCRIPTION OF PREFERRED EMBODIMENTS

The following preferred embodiments will be described in relation to a diaper. However, the inventive concept is equally applicable also to other types of absorbent articles, e.g. incontinence garments, sanitary pads, tampons, bandages, or bed protectors or the like.

Figure 1:
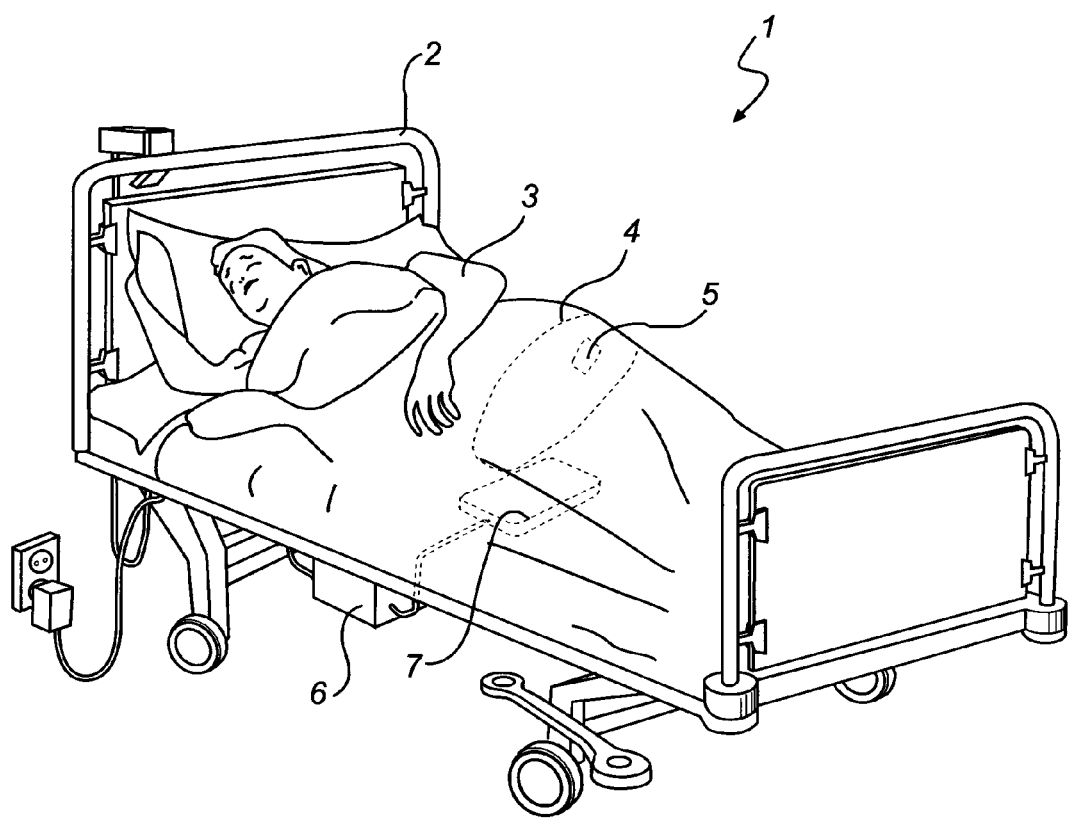
FIG. 1 illustrates a system for detecting moisture in a diaper in accordance with a first embodiment of the inventive concept.

FIG. 1 illustrates a system 1 for detecting moisture in a diaper of a first embodiment in accordance with the inventive concept. The system 1 of the first embodiment will be illustrated in the context of a bed 2 carrying a patient 3 wearing a diaper 4. The system 1 comprises a device 5 for detecting moisture in the diaper 4. The system 1 further comprises a monitoring unit 6 and an antenna 7. The monitoring unit 6 is connected to the antenna 7.

FIGS. 2a and b illustrate the device 5 in greater detail. The device 5 is provided in the form of a transponder tag. The device 5 comprises a flexible carrier having an adhesive underside (left out from the figures for increasing the clarity). The device 5 may hence be conveniently attached in the diaper 4. The device 5 is preferably attached at a location in the diaper such that the device 5 will become moist in case the patient 3 urinates or evacuates the bowel. The device 5 comprises an electrically insulating layer 9 such as a plastic film. The insulating layer 9 is provided on the upper side of the carrier. The insulating layer 9 may be coextensive with the carrier. The device 5 further comprises a resonance circuit 10 and a moisture sensitive part 13. The resonance circuit 10 and the moisture sensitive part 13 are provided on the insulating layer 9. The resonance circuit 10 may e.g. be formed by selectively etching off portions of a thin metallic layer provided on the insulating layer 9 according to principles well-known in the art.

With reference to FIGS. 2a-d, the resonance circuit 10 and the moisture sensitive part 13 will now be described in detail. The resonance circuit 10 comprises an inductor 11 and a capacitor 12. The inductor 11 is provided on a first side of the insulating layer 9. The capacitor 12 is formed by two conducting surfaces 12', 12" provided on opposite sides of the insulating layer 9. The inductor 11 is connected to the capacitor plate 12' provided on the first side of the insulating layer 9. Preferably, the first side faces the wearer.

The device 5 further comprises a moisture barrier 16 covering the inductor 11 and the capacitor 12 of the resonance circuit 10. The moisture barrier 16 prevents moisture from coming into contact with the inductor 11 and the capacitor 12.

The device 5 further comprises an outer fabric layer (left out for increasing the clarity of the figure) covering the side of the device 5 facing the patient 3 to minimize skin irritation.

As illustrated in FIG. 2a, the moisture sensitive part 13 includes two sets of conductors 14 and 14' provided on the first side of the insulating layer 9. The two sets of conductors 14, 14' form an interdigital finger structure. The conducting fingers of the two sets of conductors 14, 14' are provided in parallel to each other. The two sets of conductors 14 and 14' are separated by an insulator, such as air or a dielectric. The number of fingers, the length of the fingers and the separation of the fingers may be varied depending on e.g. the specific application, the sensitivity of the device 5 or the size of the device 5 etc.

The moisture sensitive part 13 further comprises a conducting layer 15 provided on the second side of the insulating layer 9. The conducting layer 15 is provided opposite to the two sets of conductors 14, 14'. The conducting layer 15 thus directly faces at least a part of the two sets of conductors 14, 14'. The two sets of conductors 14 and 14' are connected to the resonance circuit 10. More specifically, the first set of conductors 14 is connected to the inductor 11. The second set of conductors 14' is connected to the capacitor plate 12". The conducting layer 15 is not galvanically connected to the resonance circuit 10. By providing the conducting layer 15 opposite to the two sets of conductors 14 and 14', the conducting layer 15 may be capacity-coupled to each of the sets of conductors 14 and 14'.

In case the two sets of conductors 14 and 14' are dry, i.e. the moisture sensitive part is in a dry condition, there will be essentially no free charge carriers which may carry a current between the two sets of conductors 14 and 14'. As a result the moisture sensitive part 13 forms a capacitor of capacitance $C_a$ connected in parallel with two series connected capacitors of capacitance $C_b$ and $C_c$, wherein $C_a$ is the capacitance between the two sets of conductors 14 and 14', $C_b$ is the capacitance between the first set of conductors 14 and the conducting layer 15, and $C_c$ is the capacitance between the second set of conductors 14' and the conducting layer 15. This is illustrated in FIG. 2c.

$C_a$ is proportional, among others, to the height extension of the two sets of conductors 14 and 14' above the insulating layer 9 and inversely proportional to the separation between the fingers of the two sets of conductors 14 and 14'. $C_b$ and $C_c$ are proportional, among others, to the surface area of the conducting layer 15 and the first and second sets of conductors 14 and 14', respectively, in the plane of the insulating layer 9 and inversely proportional to the separation between the conducting layer 15 and the first and second sets of conductors 14 and 14' (i.e. the thickness of the insulating layer 9). According to the first embodiment, the height extension is much smaller than the surface area and the thickness of the insulating layer 9 is much smaller than the separation between the two sets of conductors 14 and 14'. Consequently $C_a$ will be relatively small compared to $C_b$ and $C_c$. As viewed from the resonance circuit 10, the moisture sensitive part 13 hence acts approximately as two series connected capacitances $C_b$ and $C_c$. Thus, in a dry condition the resonance frequency of the resonance circuit 10 is mainly defined by the inductance of the inductor 11 connected in series with three series connected capacitances, namely the capacitance of the capacitor 12 and the capacitances $C_b$ and $C_c$.

When the device 5 comes into contact with moisture, the moisture will penetrate the outer fabric layer and come into contact with the two sets of conductors 14 and 14'. Any charge carriers present in the fluid may then give rise to current conducting paths between the two sets of conductors 14 and 14'. The impedance between the two sets of conductors 14 and 14' will hence decrease. If a sufficient amount of charge carriers is present, the moisture sensitive part 13 will present a low impedance current path between the two sets of conductors 14 and 14' in parallel with $C_b$ and $C_c$. This is illustrated in FIG. 2d in which the capacitance $C_a$ has been replaced by a short circuit.

Thus, in a sufficiently moist condition the resonance circuit 10 will present a resonance frequency which is mainly defined by the inductance of the inductor 11 connected in series with the capacitance of the capacitor 12. This resonance frequency will be lower than the resonance frequency of the resonance circuit 10 in the dry condition. Hence, as the moisture sensitive part 13 is exposed to moisture the resonance frequency of the resonance circuit 10 will be shifted from a first resonance frequency to a second resonance frequency which is lower than the first resonance frequency.

It is to be understood that "short circuit" is a relative expression since in practice any conducting path will present some degree of resistance for a current. Thus, in this context the expression "short circuit" relates to a condition wherein the capacitances $C_b$ and $C_c$ in the moisture sensitive part 13 no longer influences the resonance frequency of the resonance circuit 10 appreciably.

The sensitivity of the device 5, may be increased by providing a salt (or other substance with similar properties in presence of moist) at the two sets of conductors 14 and 14'. When the salt comes into contact with fluid, it will dissolve and form charge carriers which may contribute to decrease the impedance between the two sets of conductors 14 and 14'.

Optionally, an absorption layer may be provided at the two sets of conductors 14 and 14'. The absorption layer may include a polymer such as a polyacrylic acid. The absorption layer may retain fluid released into the diaper 4 and thereby increase the sensitivity of the device 5.

According to a further option, the absorption layer may include a salt (or other substance with similar properties in presence of moist) to further increase the sensitivity of the device 5. By way of example, a composition of 40% A polymer and 60% salt to 60% polymer and 40% salt may be appropriate proportions in some cases.

Returning to the first embodiment, the resonance circuit 10 assumes a first resonance frequency when the moisture sensitive part 13 is in a dry condition and a second resonance frequency, which is different from the first resonance frequency, when the moisture sensitive part 13 is in a moist condition.

By transmitting a resonant electromagnetic signal to the resonance circuit 10, the resonance circuit 10 will start to resonate or oscillate at its resonance frequency. The resonance circuit 10 will continue to oscillate for a while also after electromagnetic signal has been stopped. This oscillation will generate an electromagnetic sinusoidal response signal with an exponentially decreasing amplitude envelope. This response signal may be picked-up by the antenna 7 and detected by the monitoring unit 6.

A moist condition may hence be determined based on the frequency of the response signal. Preferably, the "detection frequency" is chosen as the second resonance frequency. However, depending on the application and the desired sensitivity of the moisture detection, the detection frequency may also be chosen as a frequency between the first and the second resonance frequency.

To facilitate moist detection, the first resonance frequency and the second resonance frequency are preferably separated to such an extent that they present non-overlapping frequency bands. The specific choices of values of the inductance of the inductor 11 and the capacitances of the capacitor 12 and the moisture sensitive part 13 are preferably chosen such that the second resonance frequency falls within an appropriate license free frequency band and the first resonance frequency falls outside of this frequency band.

Returning to FIG. 1, the antenna 7 is provided at the bed 2. The antenna 7 may be provided under a mattress of the bed 2. Alternatively, the antenna 7 may be provided under an overlay mattress of the bed 2. Alternatively, the antenna 7 may be provided under a sheet or a bed linen of the bed 2. For all these alternatives, the antenna 7 is preferably provided at a central location of the bed 2. The antenna 7 is thereby provided in a well-defined relation to the patient 3, and relatively proximate to the diaper 4 and the device 5. Preferably, the antenna 7 is provided in a plastic pocket. This provides protection against moisture and enables convenient and hygienic handling of the antenna 7 during making of the bed 2. Preferably, the antenna 7 is a loop antenna. However, other types of antennas may also be used depending on the choice of frequency band and environment etc. A loop antenna may be conveniently provided in the bed 2 with minimum discomfort for the patient 3.

The monitoring unit 6 is provided at the bed 2. The monitoring unit 6 may be mounted at the bed 2. By providing the monitoring unit 6 at the bed, the patient 3 may be monitored automatically and effortlessly with a minimum work load for the nursing staff. Alternatively, the monitoring unit 6 may be a portable, handheld unit which may be provided at the bed 2 by the nursing staff at regular intervals.

The monitoring unit 6 includes transmitter circuitry and is arranged to transmit test signals to the device 5 at regular intervals (e.g. once every minute or every two minutes) and receive response signals from the device 5. The device 5 thus acts as a transponder. The monitoring unit 6 may comprise a waveform generator for generating signals to be transmitted, a signal analysis part for analyzing received signals, a DAC or other suitable circuit element for converting digital signals from the waveform generator to analog signals, and an ADC or other suitable circuit element for converting received analog signals to digital counterparts.

The monitoring unit 6 is arranged to generate and transmit a test signal. The test signal comprises a train of pulses. Preferably, the center frequency and the pulse length of the test signal is chosen such that the second resonance frequency is included in the bandwidth of the test signal. I.e. the test signal comprises a frequency component at the second resonance frequency.

According to the first embodiment, the pulse length of the test signal is such that the first resonance frequency of the resonance circuit 10 lies well outside the frequency band of the test signal. The resonance circuit 10 may hence resonate strongly in response to the test signal when the moisture detector means 13 is sufficiently moist.

The monitoring unit 6 is further arranged to listen for and detect incoming signals from the device 5. The monitoring unit 6 is further arranged to generate an indication if a signal indicating moisture is received from the device 5. The indication may comprise activating a visual or audible indicator of the monitoring unit 6. Optionally, the monitoring unit 6 may comprise a wire based or wireless communication device (e.g. Bluetooth, ZigBee, WLAN, GPRS, 3G, optical device, sound based device etc.) for transmitting a message to a networked computer or other remote data collecting device for further analysis and storage.

The monitoring unit 6 is further arranged to remove or at least decrease residual oscillations in the antenna 7. In more detail, the monitoring unit 6 is arranged to transmit a calibration signal prior to transmitting the test signal. After having transmitted the calibration signal, the monitoring unit 6 measures any residual signal oscillations present in the antenna 7 and based on this information configures its transmitter circuitry to adapt the test signal to obtain an effective attenuation of residual oscillations during the measurement phase. This increases the sensitivity and reliability of the detection.

The monitoring unit 6 is arranged to listen for a response to the test signal. The monitoring unit 6 is arranged to receive and sample incoming signals. As have been previously described, the amplitude of a response signal generated by the device 5 decays exponentially. The monitoring unit 6 is arranged to determine the amplitude envelope of a received signal and compare it to a predetermined value or envelope (e.g. an expected envelope based on a theoretical model or previous measurements). Thereby it may be determined whether the received signal originates from the device 5 or from some other source. For example, the monitoring unit 6 may be arranged to determine the exponent of the envelope and determine whether the exponent of the received signal is within a predetermined or expected range.

According to the first embodiment, the monitoring unit 6 is further arranged to, in response to a positive envelope determination, determine a frequency of the response signal. If the frequency of the response signal corresponds to or matches the detection frequency (which may be the second resonance frequency), the detection signal is generated.

The frequency may e.g. be determined by performing a Fourier analysis on the received signal, by passing the signal through a band-pass filter centered at the detection frequency or by counting the number of peak values during a time interval, or similar.

By both determining the envelope and the frequency, false detection due to noise at the detection frequency may be effectively avoided.

According to an alternative embodiment, the envelope determination may be carried out after the frequency determination.

If only a small amount of moisture is released into the diaper 4, the amount of charge carriers present at the two sets of conductors 14 and 14' may not be sufficient for shifting the resonance frequency to the detection frequency. In that case no detection signal will be generated.

Optionally, the monitoring unit 6 may be arranged to compare the signal level of received signals with a threshold to suppress noise signals and possible weak response signals from the device 5. This reduces the risk of false detections.

According to a further option the monitoring unit 6 may be arranged to generate a detection signal if the difference between the determined frequency of the response signal and the detection frequency is smaller than a frequency threshold value. A moist condition may thus be detected if a frequency of a response signal is sufficiently close to the detection frequency.

In the above reference has been made to "a dry condition" and "a moist condition". In general, there will always be some moist present in the air and consequently also in the diaper 4 and at the device 5. This is especially true in a diaper worn by a patient since there will also be some moisture released through perspiration. Thus, "a dry condition" is to be interpreted as corresponding to a level of moisture in the diaper 4 or at the device 5 when soiling (e.g. urination) has not occurred. Moreover, "a moist condition" is to be interpreted as corresponding to a level of moisture in the diaper 4 or at the device 5 wherein soiling (e.g. urination) has occurred.

Figure 4:
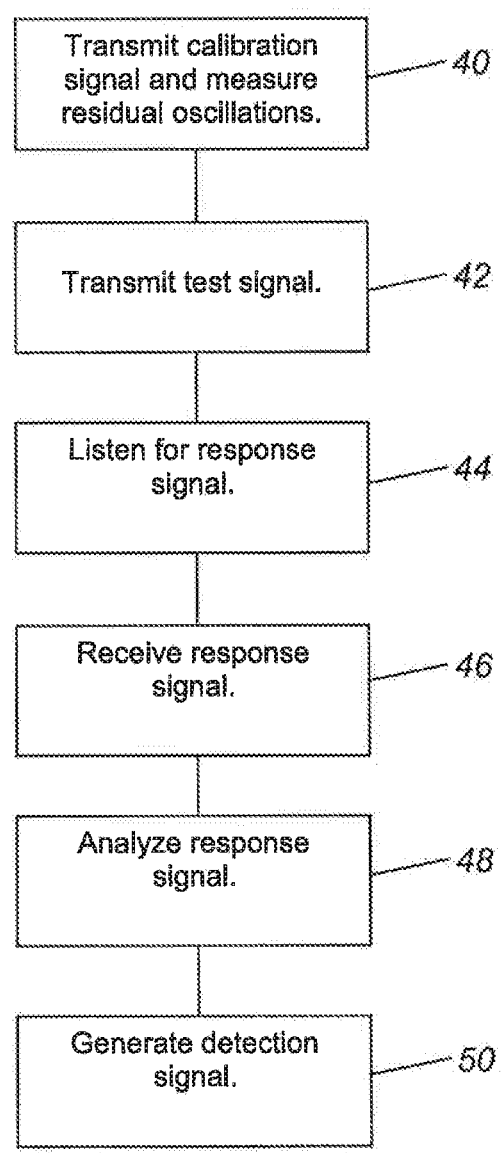
FIG. 4 is a flow chart of a method for detecting moisture in accordance with the first embodiment of the inventive concept.

With reference to FIG. 4, a method for detecting moisture in a diaper 4 in accordance with the first embodiment will now be described. The monitoring unit 6 transmits a calibration signal, measures residual oscillations in the antenna 7 generated by the calibration signal, and then configures its transmitter circuitry accordingly, as have been previously described.

Then the monitoring unit 6 transmits the test signal (box 42).

The monitoring unit 6 then listens for a response from the device 5 (box 44). If the moisture sensitive part 13 is in a moist condition the resonance circuit 10 will be excited by the test signal and start to oscillate at its resonance frequency. This oscillation generates a response signal which is received at the monitoring unit 6 (box 46).

The monitoring unit 6 analyzes the response signal (box 48). An envelope of the received signal is determined and compared to a reference envelope. Furthermore, a frequency of the response signal is determined. If the response signal presents an expected envelope and the determined frequency matches the detection frequency, the monitoring unit 6 generates a detection signal indicating that moisture has been detected (box 50). If either the envelope determination or the frequency determination is negative, no indication is generated.

Preferably the method is repeated at a suitable periodicity, e.g. every 2 minutes or every 5 minutes.

FIGS. 3a-d illustrate an alternative design of the device 5 and the resonance circuit 10. According to this alternative design, the first set of conductors 14 is connected to the inductor and the conducting layer 15 is connected to the second capacitor plate 12'. The second set of conductors 14' is not galvanically connected to the resonance circuit 10. Hence, in a dry condition the capacitance of the moisture sensitive part 13 will mainly be determined by the capacitive coupling between the conducting layer 15 and the first set of conductors 14 as illustrated in FIG. 3c.

However, in a moist condition any charge carriers present in the moisture (and/or provided at the two sets of conductors 14 and 14' and dissolved by the moisture) will give rise to alternating current conducting paths between the two sets of conductors 14 and 14'. The two sets of conductors 14 and 14' may thus form an enlarged joint conductor as illustrated in FIG. 3d. The capacitance of the moisture sensitive part 13 will hence be determined by the capacitive coupling between the conducting layer 15 and the enlarged joint conductor. Since the area of the enlarged joint conductor is larger than the area of the first set of conductors 14, the capacitance of the moisture sensitive part 13 will increase. Since the moisture sensitive part 13 is connected in series with the inductor 11 and the capacitor 12 this area increase will decrease the resonance frequency of the resonance circuit 10.

According to yet another alternative design, the first set of conductors 14 may be connected to the capacitor 12 and the conducting layer 15 may be connected to the inductor 11.

A device 5 comprising a resonance circuit 10 of any of these alternative designs may hence be used in the moisture detection method of the first embodiment.

In the above, the invention has mainly been described with reference to a few embodiments. However, as is readily appreciated by a person skilled in the art, other embodiments than the ones disclosed above are equally possible within the scope of the inventive concept, as defined by the appended claims.

The invention claimed is:

1. A system for detecting moisture at an absorbent article, the system comprising:
   a device arranged to be attached on the absorbent article and comprising a resonance circuit including a moisture sensitive part, wherein the resonance circuit has a first resonance frequency when the moisture sensitive part is in a dry condition and a second resonance frequency when the moisture sensitive part is in a moist condition, and
   a monitoring unit arranged to,
      transmit a test signal to the device,
      receive a response signal from the device,
      determine a frequency of the response signal, and
      generate a detection signal if the determined frequency corresponds to the second resonance frequency,
   wherein the moisture sensitive part includes two conductors separated by an insulator, and
   the device further includes an electrically insulating layer having a first side and a second side,
   said two conductors are provided on the first side,
   the moisture sensitive part further includes a third conductor provided on the second side opposite to the two conductors and arranged to be capacity-coupled to the two conductors, and
   the third conductor is galvanically isolated from said two conductors.

2. A system as claimed in claim 1, wherein the moisture sensitive part has a first capacitance in the dry condition and a second capacitance in the moist condition.

3. A system as claimed in claim 1, wherein the device comprises a salt which is provided at said two conductors.

4. A system as claimed in claim 1, wherein the resonance circuit comprises an inductor and a capacitor.

5. A system as claimed in claim 1, wherein the test signal comprises at least one pulse.

6. A system as claimed in claim 1, wherein the monitoring unit is arranged to:
   determine an envelope of the response signal, and
   generate the detection signal if the envelope matches a reference envelope and if the determined frequency corresponds to the second resonance frequency.

7. A method for detecting moisture at a device attached on an absorbent article, said device including a resonance circuit including a moisture sensitive part, the resonance circuit having a first resonance frequency when the moisture sensitive part is in a dry condition and a second resonance frequency when the moisture sensitive part is in a moist condition, the method comprising:
   transmitting a test signal to the device,
   receiving a response signal from the device,
   determining a frequency of the response signal, and
   generating a detection signal if the determined frequency corresponds to the second resonance frequency, wherein the moisture sensitive part includes two conductors separated by an insulator, and the device further includes an electrically insulating layer having a first side and a second side, said two conductors are provided on the first side, the moisture sensitive part further includes a third conductor provided on the second side opposite to the two conductors and arranged to be capacity-coupled to the two conductors, and the third conductor is galvanically isolated from said two conductors.

8. A method as claimed in claim 7, wherein the test signal comprises at least one pulse.

9. A method as claimed in claim 7, further comprising, in response to receiving a signal:

determining an envelope of the response signal, and generating the detection signal if the envelope matches a reference envelope and if the determined frequency corresponds to the second resonance frequency.

10. A method as claimed in claim 7, wherein the moisture sensitive part has a first capacitance in a dry condition and a second capacitance in a moist condition.

11. A system for detecting moisture at an absorbent article, the system comprising:

a device arranged to be attached on the absorbent article and comprising a resonance circuit including a moisture sensitive part, wherein the resonance circuit has a first resonance frequency when the moisture sensitive part is in a dry condition and a second resonance frequency when the moisture sensitive part is in a moist condition, and a monitoring unit arranged to, transmit a test signal to the device, receive a response signal from the device, determine a frequency of the response signal, and generate a detection signal if the determined frequency corresponds to the second resonance frequency, wherein the moisture sensitive part includes two conductors separated by an insulator, and the device further includes an electrically insulating layer having a first side and a second side, said two conductors are provided on the first side, the moisture sensitive part further includes a third conductor provided on the second side opposite to the two conductors and arranged to be capacity-coupled to the two conductors, and one conductor of said two conductors is galvanically isolated from the other conductor of said two conductors and the third conductor.

12. A system as claimed in claim 11, wherein the moisture sensitive part has a first capacitance in the dry condition and a second capacitance in the moist condition.

13. A system as claimed in claim 11, wherein the device comprises a salt which is provided at said two conductors.

14. A system as claimed in claim 11, wherein the resonance circuit comprises an inductor and a capacitor.

15. A system as claimed in claim 11, wherein the test signal comprises at least one pulse.

16. A system as claimed in claim 11, wherein the monitoring unit is arranged to:

determine an envelope of the response signal, and generate the detection signal if the envelope matches a reference envelope and if the determined frequency corresponds to the second resonance frequency.

* * * * *